(12) United States Patent
Degroote

(10) Patent No.: US 10,408,808 B2
(45) Date of Patent: Sep. 10, 2019

(54) METHOD OF CHEMICAL MARKING OF BATCHES OF CARBON DIOXIDE IN ORDER TO ENSURE TRACEABILITY

(71) Applicant: Jacques Degroote, Paris (FR)

(72) Inventor: Jacques Degroote, Paris (FR)

( * ) Notice: Subject to any disclaimer, the term of this patent is extended or adjusted under 35 U.S.C. 154(b) by 48 days.

(21) Appl. No.: 15/038,532

(22) PCT Filed: Nov. 21, 2014

(86) PCT No.: PCT/EP2014/075320
§ 371 (c)(1),
(2) Date: May 23, 2016

(87) PCT Pub. No.: WO2015/075197
PCT Pub. Date: May 28, 2015

(65) Prior Publication Data
US 2016/0290978 A1    Oct. 6, 2016

(30) Foreign Application Priority Data
Nov. 22, 2013 (FR) ..................... 13 02750

(51) Int. Cl.
*G01N 33/00* (2006.01)
*C01B 32/50* (2017.01)
*G06Q 10/08* (2012.01)

(52) U.S. Cl.
CPC .......... *G01N 33/004* (2013.01); *C01B 32/50* (2017.08); *G06Q 10/0833* (2013.01)

(58) Field of Classification Search
CPC .......... C06Q 10/0833; G06Q 10/0833; G01N 33/004
See application file for complete search history.

(56) References Cited

U.S. PATENT DOCUMENTS

| | | | |
|---|---|---|---|
| 4,551,154 A | 11/1985 | Malcosky et al. | |
| 5,677,187 A * | 10/1997 | Anderson, II | ........ C06B 23/008 436/106 |
| 7,704,746 B1 * | 4/2010 | White | ................. E21B 41/0064 436/56 |
| 2010/0208260 A1 | 8/2010 | Carr et al. | |
| 2013/0299591 A1 * | 11/2013 | Marka | .................... G06K 19/00 235/491 |
| 2015/0331002 A1 * | 11/2015 | Huber | .............. G01N 35/00732 436/56 |

FOREIGN PATENT DOCUMENTS

| | | |
|---|---|---|
| DE | 10 2011 007 332 A1 | 10/2012 |
| WO | WO 95/33121 A1 | 12/1995 |
| WO | WO 98/06930 A1 | 2/1998 |
| WO | WO 99/52708 A1 | 10/1999 |
| WO | WO 00/02029 | 1/2000 |
| WO | WO 01/25781 A2 | 4/2001 |
| WO | WO 03/010534 A2 | 2/2003 |
| WO | WO 2004/023095 A2 | 3/2004 |
| WO | WO 2007/102023 A1 | 9/2007 |
| WO | WO 2010/120895 A1 | 10/2010 |
| WO | WO 2010/132295 A1 | 11/2010 |
| WO | WO 2011/104736 A1 | 9/2011 |

OTHER PUBLICATIONS

International Search Report as issued in International Patent Application.
Wells, A.W., et al., "The use of tracers to assess leakage from the sequestration of $CO_2$ in a depleted oil reservoir, New Mexico, USA," Applied Geochemistry, vol. 22, No. 5, May 2007, XP022063723, ISSN: 0883-2927, pp. 996-1016.
Nimza, G.J., et al., "The Use of Noble Gas Isotopes for Monitoring Leakage of Geologically Stored $CO_2$," Carbon Dioxide Capture for Storage in Deep Geologic Formations, vol. 2; Geologic Storage of Carbon Dioxide with Monitoring and Verification, Elsevier, Amsterdam, pp. 1113-1128, XP008107303, ISBN: 978-0-08-044572-4 [retrieved on Sep. 18, 2007], Jan. 2005.
Myers, M., et al., "Tracers—Past, present and future applications in $CO_2$ geosequestration," Applied Geochemistry, vol. 30, Mar. 2013, pp. 125-135, XP055137947, ISSN: 0883-2927.

* cited by examiner

*Primary Examiner* — Christopher Adam Hixson
(74) *Attorney, Agent, or Firm* — Galbreath Law Offices, P.C.; John A. Galbreath

(57) ABSTRACT

A method of marking a batch of carbon dioxide including creating by a traceability computer system at least one reference for a batch of carbon dioxide, in a database of a computer system listing a plurality of batches of carbon dioxide; injecting a chemical tracer into the batch of carbon dioxide, the final concentration of the tracer in the batch being less than 1% by mass; and recording the chemical tracer formula in the traceability computer system. The formula of the chemical tracer for the batch is associated with a batch reference in the database, the chemical tracer formula having the form of a combination of proportions of at least two chemical substances.

9 Claims, No Drawings

METHOD OF CHEMICAL MARKING OF BATCHES OF CARBON DIOXIDE IN ORDER TO ENSURE TRACEABILITY

CROSS-REFERENCE TO RELATED APPLICATIONS

This is the U.S. National Stage of PCT/EP2014/075320, filed Nov. 21, 2014, which in turn claims priority to French Patent Application No. 13/02750, filed Nov. 22, 2013, the entire contents of all applications are incorporated herein by reference in their entireties.

The present invention relates to a method making it possible to produce batches of carbon dioxide ($CO_2$) that are chemically marked in order to ensure the traceability thereof throughout a logistical chain, the invention also describes a method of analyzing these batches of marked $CO_2$ in order to carry out the identification of the batch and thus to be able to access information items relative to this batch such as the owner's name, the place of production, etc.

In particular the present invention relates to a method of marking homogeneous batches of this gas combining the formulation of an original chemical tracer managed by a computer system and the injection of said tracer, of which the original composition is formulated in such a manner that the marked batch is unique and identifiable as such thanks to the use of tracer compounds used in combination. The method also includes the step of analysis of the tracers in order to identify the composition thereof. This method enables, by a comparison thereof with the database of the traceability system, the identification in a certain manner of a batch, thus enabling traceability throughout the logistical chain.

The method finds applications in numerous fields where carbon dioxide is recycled in industrial or farming uses, or simply captured and sequestered in order to meet climate challenges.

The subject matter of this invention also covers batches of $CO_2$ marked by this method.

We are witnessing the development of a circular economy through which the waste from one industry becomes the resource of the following industry in the production chain. Thus combustion gases from fossil fuels such as oil, coal, natural gas, lignite and host rock hydrocarbons, which contain a large proportion of carbon dioxide, are in practically all cases discharged into the atmosphere, where $CO_2$ contributes to trapping infrared thermal radiation and thus increasing the greenhouse effect and climatic warming. Yet carbon dioxide may also be an industrial or farming resource, until now often ignored or neglected.

But, to date, it is the waste dimension that dominates the view people have of $CO_2$.

Since $CO_2$ has been identified as one of the main greenhouse gases, its capture at the places where it is emitted, its industrial use, its storage and in certain cases its very long duration geological sequestration (several thousands of years) are essential to avoid further increasing the anthropological contribution to global warming.

When a by-product or waste from an industrial process is destined for recycling or destruction, the transferor industrial operator remains responsible for the correct compliance with regulations by the transferee up to the full completion of the recycling or destruction cycle. It could be the same for combustion gases and notably $CO_2$. The transfer of ownership of a gas identified as a waste entails the responsibility of the transferor to check that the regulations are correctly respected by the transferee, either by the destruction of the waste, its storage or its sequestration according to the regulations of the place, or by its recycling that is to say its requalification as a product, but in this case, this reassignment must comply with regulations which, notably, require that the elements necessary for its original traceability are attached to the batch of gas.

This case applies particularly to processes for capturing industrial $CO_2$ for the purposes of reuse or environmental sequestration which give rise to fiduciary exchanges or tax exemptions for considerable sums.

Several processes and apparatuses exist for capturing $CO_2$ which make it a specific resource to be transported to its place of use or storage. This gas may be transported after compression and/or liquefaction using the transport vectors generally used for gases (ship, pipeline). However, all raw materials supplied as inputs to industry, such as any material considered as a waste, must be subject to traceability throughout its transport, from its place of capture or extraction to its place of final use. It is important that all industries using $CO_2$ as an input are able to know the nature and the origin in a guaranteed and approved manner. Each batch must be characterized and identifiable.

As an example, this gas is in volume terms the foremost fertilizer in the world used by the plant biosphere thanks to photosynthesis, coming within the framework of the carbon cycle. Certain emerging applications such as the production of microalgae consume a lot of $CO_2$. Other industrial sectors, in the carbon chemistry field, use this gas in strongly growing proportions.

The industrial use of $CO_2$, beyond its storage in view of its sequestration (CCS, "Carbon Capture and Storage"), may enter into numerous application fields: fizzy drinks, inert atmospheres, extinguishers, refrigerant fluids, dry ice, etc. $CO_2$ in its supercritical phase is a solvent used in the food processing, pharmaceutical and cosmetic industries. $CO_2$ is also used in greenhouse agriculture, with the aim of increasing yields by over-concentration of $CO_2$ in the confined enclosure.

In the case of geological sequestration of $CO_2$, it must be the subject of an approval and an affidavit, which must enable, according to the regulations in force, the issuance of a certificate that can have a fiduciary value, which can be collateralized against rights known as "polluting rights", emission quotas or partial or total exonerations of taxes on polluting activities, but also be subject to a financial compensation within the framework of regulations on exchanges of carbon rights (whether for countries having put in place "right to pollute" exchange mechanisms, or within the scope of the Clean Development Mechanisms put in place by the Kyoto agreements).

STATE OF THE PRIOR ART

The prior art makes it possible to inject a gaseous compound to mark the gas and to enable the detection thereof directly by users or by means of a probe connected to a measuring apparatus. Protocols exist for adding an olfactory tracer enabling the detection of leaks, as is the case for the use of combustible gases intended for private individuals (town gas, butane cylinders, distribution of LPG fuel, etc.) in which sulfur containing gases, non-toxic and with very low perception thresholds by the human nose, are used.

This method has been generalized in natural gas distribution circuits for domestic use. In the event of leakage of this combustible gas, the presence of the adjuvant gas, easily recognizable by its odor, makes it possible to give warning of the risk of explosion. This method thus makes it possible to identify the hazardous character of a gas but in no case does it make it possible to identify the gas (methane, butane or other), to specify the place of its synthesis or its capture, to identify the supplier, and even less to respond to an identification by batch. This method is not used for $CO_2$.

Processes enabling the chemical marking of gases already exist:

- As is the case for the marking of natural gas stored in underground nappes using tracers synthetized by catalytic reaction of the gas such as ethylene, propylene, hydrogen or carbon monoxide as described in the document WO2004023095; in the invention according to this process, the gas concerned is a natural mineral resource of great value and the use of the tracer serves to determine the quantity of natural gas in a storage layer and/or to follow the movements of the gas through rocks, as is the case by perfusion of a reactive isotopic marker gas in a mass spectrometry apparatus as described in the document WO2010120895,
- such as the marking of fluids, by adjunction of fluorescent microparticles such as taught in the document WO9952708, creating a diphasic medium (liquid-solid or gas-solid) which may be separated,
- such as the use of solid tracers, composed of metal elements or salts thereof, injected into an underground formation containing oil or natural gas, described in the document WO2007102023,
- such as systems for injecting tracers into oil and gas bore holes which are then detected to deduce therefrom the depths concerned as described in the documents WO9806930 and WO9533121,
- such as the use of rare gases (document WO03010534) or a radioactive isotope of carbon (document WO2010132295) to detect underground movements and leakages in geological $CO_2$ sequestration installations,
- such as the addition of an artificial tracer gas ($SF_6$ or $C_2HF_5$) to methane stored in a dried up underground reservoir in order to prove the ownership thereof, as taught in the document U.S. Pat. No. 4,551,154.

It is possible to produce by chemical reaction gas mixtures with several components at the moment of the injection in a flow of gas such as the process described in the document WO0125781, but this method does not make it possible to be able to certify the exact composition of the products of the reaction.

These methods make it possible to follow the advance of a gas in a circuit or in an underground storage, they also make it possible to distinguish an industrial sourced gas from a naturally sourced gas. But it is impossible to be able to create on demand batches of different gases comprising original and stable markers, capable of being coupled to a secure traceability system.

Furthermore, processes for detecting gas tracers exist:
- direct detection by humans is possible for tracers having a strong olfactory fingerprint, such as mercaptans used as olfactory tracers for warning purposes in natural gas networks,
- indirect detection via a colored chemical reaction involving the same mercaptans as evoked in the document WO0002029,
- the detection of fluorescent tracers for pinpointing leakages in air conditioning circuits is well known to those skilled in the art, fluorescence is also used to mark hydrocarbon reservoirs according to the application US20100208260,
- the detection of tracer gases at very low concentration via a specific chemical sensor such as used in the document DE102011007332.

It is more generally possible to mark containers of gases, in particular pressurized gases, by everyday mechanical systems for individual marking and identification on gas cylinders or tanks; the document WO2011104736 describes a particular case thereof. Nevertheless, the notion of identification of homogeneous gas batch is then only made by the identification of the container, but it is not the gas in itself which is the subject of an original serialization, batch by batch. Thus, in the case of transfer of a gas from one container to another, or passage through a liquefaction/gasification installation, the traceability chain is broken, and nothing precludes either emptying then refilling the container with another batch of gas.

The method of production of a marked batch of $CO_2$ consists in injecting into batches of gas from an industrial process producing $CO_2$ (for example a combustion, a fermentation), directly or after treatment (scrubbing, enrichment, separation), a mixture of marker chemical compounds of which the composition is created specifically for the batch to be marked, in order to enable the physical or chemical identification thereof throughout its logistical chain, even in the case of change of state, of transshipment, of change of container, etc. The transport of this batch of gas may take place in confined enclosures, by land, river or sea route or by pipeline.

The embodiment makes it possible to envisage the assembly of several batches by mixing thus constituting a new homogeneous batch, of which the composition of the tracer, then being itself the combination, weighted by the assembled quantities, of the tracers of each batch in the mixture, will be unique and characteristic of this new batch thereby composed.

The homogeneous batch of $CO_2$ marked in a unique manner is composed:
- for a very majority part (at least 90% by weight), of carbon dioxide, for example from the combustion of fossil resources such as coal, oil and natural gas,
- for a minority part (less than 5% by weight), of a tracer in the form of a combination of several (at least two) chemical compounds.

According to an embodiment, the method of marking of a batch of carbon dioxide, includes the steps of:
- Creation by a traceability computer system of a reference for a batch of carbon dioxide by a computer system,
- Injection of a chemical tracer into the batch of carbon dioxide, the final concentration of the tracer in the batch being less than 1% by weight,
- Recording of the chemical tracer formula in the traceability computer system,
- characterized by the fact that the chemical tracer formula is specific to the batch and having the form of a combination of at least two chemical substances.

According to an advantageous embodiment, the concentration of the substances of the chemical tracer in the marked batch of $CO_2$ is less than 0.1% (1000 ppm).

To produce the tracer, chemical compounds selected from the following may advantageously be used:
- halogen containing compounds or hydrocarbons, such as, but not limited to, sulfur hexafluoride, hydrofluorocarbons, hydrochlorofluorocarbons, chlorofluorocarbons and hydrochlorocarbons,
- oxygen containing organic compounds such as those belonging to the family of alcohols, aldehydes, ketones, ethers, carboxylic acids, sulfur containing organic compounds such as thiols or nitrogen compounds.

For economic reasons the tracer compounds will be preferentially selected from compounds combining a very low detection threshold (typically of the order of ppm, or even much less) and a moderate cost price.

Advantageously, the compounds may be enantiomers or diastereoisomers present in non-racemic proportions, their physical and chemical properties being very similar, the ratio between compounds changes little during the transformations undergone throughout the logistical chain of the batch of $CO_2$.

Advantageously, two at least of the compounds may be enantiomers or diastereoisomers or only differ by their isotopic composition.

Chemical compounds enriched in stable natural isotopes such as deuterium or carbon 13 may also be used to implement the method, uniformly or at certain very precise positions of the molecules.

It is also possible to use fluorescent chemical compounds to implement the method.

The subject matter of the invention includes the use of a computer system, preferably highly secured, intended to:
- reference each batch, with information items such as the owner of the gas, the period of capture of the gas constituting the batch, the volumetry of gas, the industrial installation that is the source of the batch, etc.,
- conceive a chemical formula of tracer for this batch,
- associate this formula with the batch,
- remotely manage its production and its injection into the batch, via the control of an automaton established in the industrial installation and equipped with reservoirs of chemical substances and solenoid valves,
- if need be, manage the assembly of several batches in order to constitute a larger batch, the tracer of this assembled batch being the linear combination of the tracers of each individual batch,
- record each event of the logistical chain of the marked batch of $CO_2$ thereby constituted,
- analyze the results of the physical-chemical analyses carried out for the purposes of identification of a batch of $CO_2$ and compare them with the theoretical composition of the tracer and conclude thanks to an expert system (taking account of the different transformations undergone by the batch and being able to affect the composition of the tracer) on the identification of the batch.

According to an embodiment, the injection is carried out in liquefied and compressed gas.

According to another embodiment, the injection is carried out in gaseous form.

The computer system may take into account operating uncertainties, notably at the moment of the injection (malfunction of a valve, empty cylinder, etc.) by automatically recalculating a new tracer formula.

The computer system is certified and auditable by approved control organizations so as to be able to be used as proof within the framework of regulation and compensation systems linked to $CO_2$ (taxes on polluting activities, carbon taxes, emission quotas, specific development mechanisms, etc.).

According to an embodiment, a marked batch of carbon dioxide is obtained, containing a chemical tracer and referenced in a traceability computer system, characterized by the fact that:
- the batch contains a minimum of 90% by weight of carbon dioxide,
- the chemical tracer is composed of a mixture of at least two chemical substances, the concentration of the tracer in the batch being less than 1% by weight,
- the traceability computer system associates in a database the marked batch with the proportion of the different components of the tracer and with information items on the origin of the carbon dioxide,
- the batch may be analyzed in order to identify the nature and the proportion of the substances composing the chemical tracer.

In a particular embodiment of the batch described above, at least one of the chemical substances of the tracer is a halogen containing hydrocarbon, a sulfur, nitrogen or oxygen compound.

In another particular embodiment of the batch described above, at least two of the chemical substances of the tracer are enantiomers or diastereoisomers or only differ by their isotopic composition.

Analyses specific to the detection of the chemical substances composing the mixture and to the identification of the batch are carried out preferentially by mass spectrometry or gas phase chromatography or by nuclear magnetic resonance. Other analytical techniques may be employed such as spectroscopy (visible, UV, IR or FT-IR). Alternatively, chromatography, electrophoresis, may be used, notably with a column comprising a chiral phase thereby making it possible to separate enantiomer or diastereoisomer molecules.

Alternatively, the physical-chemical analysis method is carried out by a combination of these analytical methods.

ADVANTAGES BROUGHT BY THE INVENTION

The method has several advantages compared to the prior art, particularly in that it makes it possible to produce as many different batches as necessary thanks to the combinations in variable proportions of the different chemical compounds used as tracers.

This system may form part of a complete gas traceability device and enable notably the assembly of different batches during a change of mode of transport or vectors, and a break of load. Knowledge of the composition of each of the marked batches makes it possible to deduce therefrom the resulting composition after mixing and to identify it in as reliable manner as each of the original batches.

This system enabling the traceability of batches of $CO_2$ provides a response to industrial definitions of requirements on the nature of the gas, the volume of the batch, the destination of the batch, the location of the batch, the origin of the batch, even when the place of production of the batch and the place of use are several thousands of kilometers apart.

The system may advantageously be used by industrial concerns wishing to prove that the $CO_2$ produced by their installation has indeed been reused, recycled or buried.

The system may also serve for an industrial user of $CO_2$ and that wishes to certify that the gas used has a given characteristic: generated by a clean or biological process (e.g. a fermentation), produced on a given territory, etc. This functionality may interest industrial concerns of the food processing sector that wish to control the quality of their inputs including gaseous inputs (biological production, microalgae farming, etc.); for such an application, the tracer compounds will be selected by authorized natural compounds or by food standards.

The invention claimed is:

1. A method of marking batches of carbon dioxide, wherein each batch of carbon dioxide is recycled carbon dioxide in industrial or farming use or is captured and sequestered carbon dioxide for meeting climate criteria, the method comprising:
   a. creating, by a traceability computer system, a first reference for a first batch of carbon dioxide and a second reference for a second batch of carbon dioxide in a database of a computer system listing a plurality of batches of carbon dioxide;
   b. injecting a first chemical tracer into the first batch of carbon dioxide and a second chemical tracer into the second batch of carbon dioxide, a final concentration of the tracer in each batch being less than 1% by weight, and
   c. recording a formula of the first chemical tracer and a formula of the second chemical tracer in the traceability computer system, the formula of the first chemical tracer and the formula of the second chemical tracer being associated, respectively, with the first reference and the second reference in the database, each chemical tracer formula being formed as a combination of proportions of at least two chemical substances;
   d. mixing the first batch of carbon dioxide with the second batch of carbon dioxide;
   e. recording the chemical tracer formula of the batch formed by the mixture of the first batch of carbon dioxide with the second batch of carbon dioxide in the traceability computer system, the proportions of chemical substances of the first chemical tracer and the second chemical tracer defining a new proportion of chemical substances of the batch formed by the mixture.

2. The method according to claim 1, wherein at least one of the chemical substances is a halogen containing hydrocarbon.

3. The method according to claim 1, wherein at least one of the chemical substances is a sulfur or nitrogen compound.

4. The method according to claim 1, wherein at least one of the substances includes an alcohol, ether, carboxylic acid, aldehyde or ketone functional group.

5. The method according to claim 1, wherein at least two of the substances of the tracer are enantiomers or diastereoisomers or only differ by their isotopic composition.

6. The method according to claim 1, wherein the injection is carried out in liquefied or compressed gas.

7. The method according to claim 1, wherein the injection is carried out in gaseous form.

8. The method according to claim 1, wherein the concentration of the substances of the chemical tracer in the marked batch of $CO_2$ is less than 0.1% (1000 ppm) by weight.

9. The method according to claim 1, wherein the at least one reference comprises one or more of an owner of the carbon dioxide, a period of capture of the carbon dioxide constituting the batch, a volumetry of the carbon dioxide, and an industrial installation that is a source of the batch.

* * * * *